United States Patent
Whelan et al.

(10) Patent No.: US 12,271,426 B2
(45) Date of Patent: Apr. 8, 2025

(54) METHOD, SYSTEM, AND COMPUTER PROGRAM PRODUCT FOR GENERATING A CUSTOMIZED PHOTOCHROMIC OPTICAL ARTICLE RECOMMENDATION

(71) Applicant: Transitions Optical, Ltd., Tuam (IE)

(72) Inventors: Sean D. Whelan, Kilcolgan (IE); Pascale Tardieu, Dublin (IE); Christopher J. Baldy, Murrysville, PA (US)

(73) Assignee: Transitions Optical, Ltd., Tuam (IE)

(*) Notice: Subject to any disclaimer, the term of this patent is extended or adjusted under 35 U.S.C. 154(b) by 94 days.

(21) Appl. No.: 17/427,483

(22) PCT Filed: Jan. 30, 2020

(86) PCT No.: PCT/EP2020/052213
§ 371 (c)(1),
(2) Date: Jul. 30, 2021

(87) PCT Pub. No.: WO2020/157160
PCT Pub. Date: Aug. 6, 2020

(65) Prior Publication Data
US 2022/0156326 A1     May 19, 2022

Related U.S. Application Data

(60) Provisional application No. 62/799,935, filed on Feb. 1, 2019.

(51) Int. Cl.
*G06F 16/9035*     (2019.01)
*A61B 3/04*     (2006.01)
(Continued)

(52) U.S. Cl.
CPC ............ *G06F 16/9035* (2019.01); *A61B 3/04* (2013.01); *A61B 3/06* (2013.01); *G06F 16/907* (2019.01)

(58) Field of Classification Search
CPC ..... G06F 16/9035; G06F 16/907; A61B 3/04; A61B 3/06; G01M 11/0285
See application file for complete search history.

(56) References Cited

U.S. PATENT DOCUMENTS 7,980,692 B2 * 7/2011 Fisher .................... G02C 7/061
                                                 351/159.74
9,904,949 B1 * 2/2018 Tavernier ........... G06Q 30/0631
(Continued)

FOREIGN PATENT DOCUMENTS

CN        109241076 A      1/2019
EP          2797011 A1    10/2014
(Continued)

*Primary Examiner* — Robert W Beausoliel, Jr.
*Assistant Examiner* — Susan F Rayyan
(74) *Attorney, Agent, or Firm* — The Webb Law Firm

(57) ABSTRACT

A method of generating a customized photochromic optical article recommendation for a user includes: for each of a plurality of photochromic optical articles, determining a plurality of performance attributes; receiving, from a user device, feedback data associated with each of the plurality of performance attributes; based on the plurality of performance attributes and the feedback data, generating, for each of the plurality of photochromic optical articles, a compatibility score; and based on the compatibility score for each of the plurality of photochromic optical articles, generating a user-specific recommendation including at least one of the plurality of photochromic optical articles. A system and computer program product for generating a customized photochromic optical article recommendation for a user are also disclosed.

18 Claims, 4 Drawing Sheets

(51) Int. Cl.
*A61B 3/06* (2006.01)
*G06F 16/907* (2019.01)

(56) References Cited

U.S. PATENT DOCUMENTS

| | | | |
|---|---|---|---|
| 10,031,350 B2 | 7/2018 | Fonte et al. | |
| 10,043,207 B2 | 8/2018 | Inoue et al. | |
| 10,091,554 B1* | 10/2018 | Newell | H04N 21/4532 |
| 10,693,981 B2* | 6/2020 | Galai | G06F 16/9535 |
| 11,494,666 B2* | 11/2022 | Golbandi | G06N 5/04 |
| 11,525,757 B2* | 12/2022 | Baillet | G01N 21/00 |
| 2009/0319337 A1* | 12/2009 | Xie | G06Q 10/063 705/26.1 |
| 2009/0327624 A1* | 12/2009 | Tamura | G06F 11/1435 711/158 |
| 2010/0296055 A1 | 11/2010 | Esser et al. | |
| 2011/0063571 A1* | 3/2011 | Duffy | A61B 3/06 351/239 |
| 2011/0255051 A1* | 10/2011 | McCabe | G02C 7/12 351/159.63 |
| 2012/0200847 A1 | 8/2012 | Hall | |
| 2013/0088490 A1* | 4/2013 | Rasmussen | G06T 17/00 345/421 |
| 2014/0279179 A1* | 9/2014 | Balter | A61B 3/0041 705/26.5 |
| 2015/0097855 A1* | 4/2015 | Dotan | G02C 13/003 351/159.6 |
| 2015/0242929 A1* | 8/2015 | Wilkinson | A43D 3/024 705/26.7 |
| 2017/0255262 A1* | 9/2017 | Liu | G06F 3/015 |
| 2017/0371178 A1 | 12/2017 | Crespo et al. | |
| 2018/0025005 A1* | 1/2018 | Cao | H04L 67/535 707/734 |
| 2018/0114063 A1* | 4/2018 | Wexler | G06N 5/04 |
| 2018/0218430 A1* | 8/2018 | Prendki | G06Q 30/0641 |
| 2018/0239773 A1 | 8/2018 | Shaw et al. | |
| 2018/0252942 A1* | 9/2018 | Gamliel | A61B 3/0025 |
| 2019/0086691 A1* | 3/2019 | Lappe | G02C 7/027 |
| 2019/0266185 A1* | 8/2019 | Rao | H04N 21/4758 |
| 2019/0271612 A1* | 9/2019 | Baillet | G01J 3/00 |
| 2021/0055217 A1* | 2/2021 | Blackburn | G02B 1/043 |

FOREIGN PATENT DOCUMENTS

| | | |
|---|---|---|
| JP | 2010517088 A | 5/2010 |
| JP | 2011192189 A | 9/2011 |
| JP | 2016537716 A | 12/2016 |
| JP | 201741281 A | 2/2017 |
| WO | 2017025605 A1 | 2/2017 |
| WO | 2018121877 A1 | 7/2018 |

\* cited by examiner

METHOD, SYSTEM, AND COMPUTER PROGRAM PRODUCT FOR GENERATING A CUSTOMIZED PHOTOCHROMIC OPTICAL ARTICLE RECOMMENDATION

CROSS-REFERENCE TO RELATED APPLICATIONS

This application is the United States national phase of PCT/EP2020/052213 filed Jan. 30, 2020, and claims priority to U.S. Provisional Application No. 62/799,935 filed Feb. 1, 2019, the disclosures of which are hereby incorporated by reference in their entirety.

FIELD

The present disclosure relates to a system, method, and computer program product for generating a customized photochromic optical article recommendation for a user.

BACKGROUND

Performance attributes associated with various commercially available photochromic optical articles differ from product to product. While certain photochromic optical articles may exhibit better performance for certain particular performance attributes compared to competing photochromic optical articles, that same photochromic optical article may exhibit poorer performance with respect to other performance attributes. This fact makes comparing and analyzing competing photochromic optical articles and generating recommendations for a user regarding the best photochromic optical articles for that particular user difficult.

SUMMARY

Provided is a method of generating a customized photochromic optical article recommendation for a user, including: for each of a plurality of photochromic optical articles, determining, with at least one processor, a plurality of performance attributes; receiving, from a user device and with at least one processor, feedback data associated with each of the plurality of performance attributes; based on the plurality of performance attributes and the feedback data, generating, with at least one processor and for each of the plurality of photochromic optical articles, a compatibility score; and based on the compatibility score for each of the plurality of photochromic optical articles, generating, with at least one processor, a user-specific recommendation including at least one of the plurality of photochromic optical articles.

Also provided is a system for generating a customized photochromic optical article recommendation for a user, including: a database configured to store a plurality of performance attributes for each of a plurality of photochromic optical articles; and at least one processor programmed or configured to: determine a plurality of performance attributes for each of a plurality of photochromic optical articles; receive, from a user device, feedback data associated with each of the plurality of performance attributes; based on the plurality of performance attributes and the feedback data, generate, for each of the plurality of photochromic optical articles, a compatibility score; and based on the compatibility score for each of the plurality of photochromic optical articles, generate a user-specific recommendation including at least one of the plurality of photochromic optical articles.

Also provided is a computer program product for generating a customized photochromic optical article recommendation for a user, the computer program product including at least one non-transitory computer-readable medium including one or more instructions that, when executed by at least one processor, cause the at least one processor to: determine a plurality of performance attributes for each of a plurality of photochromic optical articles; receive, from a user device, feedback data associated with each of the plurality of performance attributes; based on the plurality of performance attributes and the feedback data, generate, for each of the plurality of photochromic optical articles, a compatibility score; and based on the compatibility score for each of the plurality of photochromic optical articles, generate a user-specific recommendation including at least one of the plurality of photochromic optical articles.

The present invention can be further characterized by one or more of the following non-limiting clauses.

Clause 1: A method of generating a customized photochromic optical article recommendation for a user, comprising: for each of a plurality of photochromic optical articles, determining, with at least one processor, a plurality of performance attributes; receiving, from a user device and with at least one processor, feedback data associated with each of the plurality of performance attributes; based on the plurality of performance attributes and the feedback data, generating, with at least one processor and for each of the plurality of photochromic optical articles, a compatibility score; and based on the compatibility score for each of the plurality of photochromic optical articles, generating, with at least one processor, a user-specific recommendation comprising at least one of the plurality of photochromic optical articles.

Clause 2: The method of clause 1, further comprising: determining, with at least one processor, a living environment associated with the user, wherein the compatibility score is based at least partially on the living environment associated with the user.

Clause 3: The method of clause 1 or 2, further comprising: determining, with at least one processor, an optical characteristic associated with an eye of the user, wherein the compatibility score is based at least partially on the optical characteristic associated with the eye of the user.

Clause 4: The method of any one of clauses 1-3, wherein each of the plurality of photochromic optical articles comprises at least one of the following: a lens, goggles, a visor, and a face shield.

Clause 5: The method of any one of clauses 1-4, wherein the plurality of performance attributes comprise at least one of the following: outdoor darkness, indoor clarity, speed to dark, speed to clear, indoor blue light protection, outdoor blue light protection, ultraviolet radiation protection, reactivity in indirect sunlight, time-based performance, in-car activation, and color consistency.

Clause 6: The method of any one of clauses 2-5, wherein the living environment associated with the user comprises at least one of outdoor air temperature and exposure to radiation.

Clause 7: The method of any one of clauses 3-6, wherein the optical characteristic associated with the eye of the user comprises a level of glare sensitivity of the user.

Clause 8: A system for generating a customized photochromic optical article recommendation for a user, comprising: a database configured to store a plurality of performance attributes for each of a plurality of photochromic optical articles; and at least one processor programmed or configured to: determine a plurality of performance attributes for each of a plurality of photochromic optical articles; receive, from a user device, feedback data associated with each of the plurality of performance attributes; based on the plurality of performance attributes and the feedback data, generate, for each of the plurality of photochromic optical articles, a compatibility score; and based on the compatibility score for each of the plurality of photochromic optical articles, generate a user-specific recommendation comprising at least one of the plurality of photochromic optical articles.

Clause 9: The system of clause 8, wherein the at least one processor is further programmed or configured to: determine a living environment associated with the user, wherein the compatibility score is based at least partially on the living environment associated with the user.

Clause 10: The system of clause 8 or 9, wherein the at least one processor is further programmed or configured to: determine an optical characteristic associated with an eye of the user, wherein the compatibility score is based at least partially on the optical characteristic associated with the eye of the user.

Clause 11: The system of any one of clauses 8-10, wherein each of the plurality of photochromic optical articles comprises at least one of the following: a lens, goggles, a visor, and a face shield.

Clause 12: The system of any one of clauses 8-11, wherein the plurality of performance attributes comprise at least one of the following: outdoor darkness, indoor clarity, speed to dark, speed to clear, indoor blue light protection, outdoor blue light protection, ultraviolet radiation protection, reactivity in indirect sunlight, time-based performance, in-car activation, and color consistency.

Clause 13: The system of any one of clauses 9-12, wherein the living environment associated with the user comprises at least one of outdoor air temperature and exposure to radiation.

Clause 14: The system of any one of clauses 10-13, wherein the optical characteristic associated with the eye of the user comprises a level of glare sensitivity of the user.

Clause 15: A computer program product for generating a customized photochromic optical article recommendation for a user, the computer program product comprising at least one non-transitory computer-readable medium including one or more instructions that, when executed by at least one processor, cause the at least one processor to: determine a plurality of performance attributes for each of a plurality of photochromic optical articles; receive, from a user device, feedback data associated with each of the plurality of performance attributes; based on the plurality of performance attributes and the feedback data, generate, for each of the plurality of photochromic optical articles, a compatibility score; and based on the compatibility score for each of the plurality of photochromic optical articles, generate a user-specific recommendation comprising at least one of the plurality of photochromic optical articles.

Clause 16: The computer program product of clause 15, wherein the one or more instructions further cause the at least one processor to: determine a living environment associated with the user, wherein the compatibility score is based at least partially on the living environment associated with the user.

Clause 17: The computer program product of clause 15 or 16, wherein the one or more instructions further cause the at least one processor to: determine an optical characteristic associated with an eye of the user, wherein the compatibility score is based at least partially on the optical characteristic associated with the eye of the user.

Clause 18: The computer program product of any one of clauses 15-17, wherein each of the plurality of photochromic optical articles comprises at least one of the following: a lens, goggles, a visor, and a face shield.

Clause 19: The computer program product of any one of clauses 15-18, wherein the plurality of performance attributes comprise at least one of the following: outdoor darkness, indoor clarity, speed to dark, speed to clear, indoor blue light protection, outdoor blue light protection, ultraviolet radiation protection, reactivity in indirect sunlight, time-based performance, in-car activation, and color consistency.

Clause 20: The computer program product of any one of clauses 16-19, wherein the living environment associated with the user comprises at least one of outdoor air temperature and exposure to radiation.

Clause 21: The computer program product of any one of clauses 17-20, wherein the optical characteristic associated with the eye of the user comprises a level of glare sensitivity of the user.

The features that characterize the present invention are pointed out with particularity in the claims, which are annexed to and form a part of this disclosure. These and other features, operating advantages, and the specific objects obtained by use will be more fully understood from the following detailed description in which non-limiting embodiments are illustrated and described.

DETAILED DESCRIPTION

Figure 1:
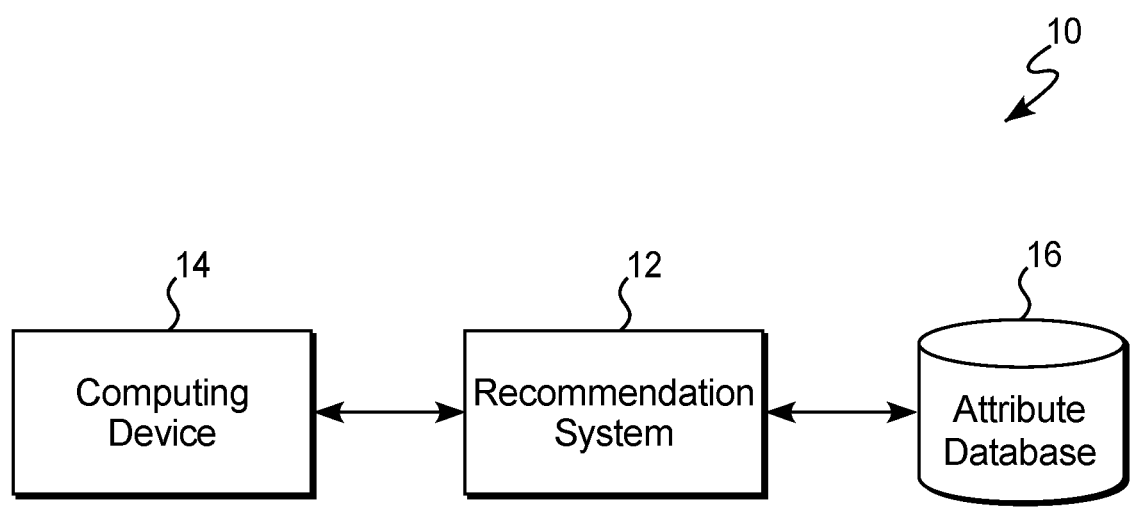
FIG. 1 shows a system for generating a customized photochromic optical article recommendation for a user.

For purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

As used herein, the articles "a", "an", and "the" include plural referents unless otherwise expressly and unequivocally limited to one referent.

As used herein, the term "includes" is synonymous with "comprises".

As used herein, "at least one of" is synonymous with "one or more of", whether the elements are listed conjunctively or disjunctively. For example, phrases such as "at least one of the following: A, B, and C" or "at least one of the following: A, B, or C" each mean any one of A, B, or C, or any combination of any two or more of A, B, or C. For example, A alone; or B alone; or C alone; or A and B; or A and C; or B and C; or all of A, B, and C.

As used herein, the term "photochromic" and similar terms, such as "photochromic compound," means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "actinic radiation" means electromagnetic radiation that is capable of causing a response in a material, such as, but not limited to, transforming a photochromic material from one form or state to another as will be discussed in further detail herein.

As used herein, and unless stated otherwise or otherwise limited, the term "photochromic material" includes thermally reversible photochromic materials and compounds and non-thermally reversible photochromic materials and compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein, to modify the term "state," the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, the photochromic compounds of the present disclosure can have a different absorption spectrum in each of the first and second state. For example, while not limiting herein, a photochromic compound of the present disclosure can be clear in the first state and colored in the second state. Alternatively, a photochromic compound of the present disclosure can have a first color in the first state and a second color in the second state.

As used herein, the term "optical" means pertaining to or associated with light and/or vision. For example, the optical article or element or device can be chosen from ophthalmic articles, elements and devices; display articles, elements and devices; windows; mirrors; or active and passive liquid crystal cell articles, elements and devices.

As used herein, the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses, goggles, visors, or face shields.

As used herein, the term "display" means the visible or machine-readable representation of information in words, numbers, symbols, designs, or drawings. Non-limiting examples of display elements include screens, monitors, and security elements, such as security marks.

As used herein, the term "window" means an aperture adapted to permit the transmission of radiation therethrough. Non-limiting examples of windows include automotive and aircraft transparencies, windshields, filters, shutters, and optical switches.

As used herein, the term "mirror" means a surface that specularly reflects a large fraction of incident light.

As used herein, the term "liquid crystal cell" refers to a structure containing a liquid crystal material that is capable of being ordered. A non-limiting example of a liquid crystal cell element is a liquid crystal display.

As used herein, the terms "communication" and "communicate" may refer to the reception, receipt, transmission, transfer, provision, and/or the like, of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection (e.g., a direct communication connection, an indirect communication connection, and/or the like) that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and communicates the processed information to the second unit. In some non-limiting embodiments or aspects, a message may refer to a network packet (e.g., a data packet and/or the like) that includes data. It will be appreciated that numerous other arrangements are possible.

As used herein, the term "computing device" may refer to one or more electronic devices capable of processing data. The computing device may be a mobile device. As an example, a mobile device may include a cellular phone (e.g., a smartphone or standard cellular phone), a portable computer, a wearable device (e.g., watches, glasses, lenses, clothing, and/or the like), a personal digital assistant (PDA), and/or other like devices. The computing device may be a desktop computer, kiosk, or other non-mobile computer. Furthermore, the terms "computer" or "computing device" may refer to any device that includes the necessary components to receive, process, and output data, and normally includes a display, a processor, a memory, an input device, and a network interface.

The present disclosure is directed to a method, system, and computer program product for generating a customized photochromic optical article recommendation for a user. Non-limiting examples of photochromic optical articles include lenses (e.g., corrective lenses, non-corrective lenses, contact lenses, intra-ocular lenses, magnifying lenses, or protective lenses), goggles, visors, or face shields that exhibit photochromic properties. Other examples of photochromic optical articles include automotive transparencies, windows, display elements and devices, wearable displays, mirrors, and active and passive liquid crystal cell elements and devices that exhibit photochromic properties. The photochromic optical articles may include any art-recognized optical substrates, including organic thermosets, thermoplastics, or mineral glasses with photochromic properties, with or without added attributes such as anti-reflective coatings and/or hard multi coating (HMC) or the like. The photochromic dyes may be incorporated by any means, including but not limited to, coating, overmolding, lamination, imbibition, in mass polymerization, or printing.

The present disclosure may include a recommendation system configured to generate a user-specific recommendation of at least one photochromic optical article for a user. The user-specific recommendation may be based on feedback data from the user and performance attributes associated with the photochromic optical articles. The recommendation system may generate a compatibility score which quantifies the compatibility of each photochromic optical article with user preferences from the feedback data (and/or other data as described hereinafter). The compatibility score may consider the living environment of the user to more accurately determine the most compatible photochromic optical article. The compatibility score may consider an optical characteristic associated with the eyes of the user, such as a measured optical characteristic, to more accurately determine the most compatible photochromic optical article. In this way, the system, method, and computer program product of the present disclosure determines for the user which photochromic optical article(s) is most suitable for that individual user.

Figure 2:
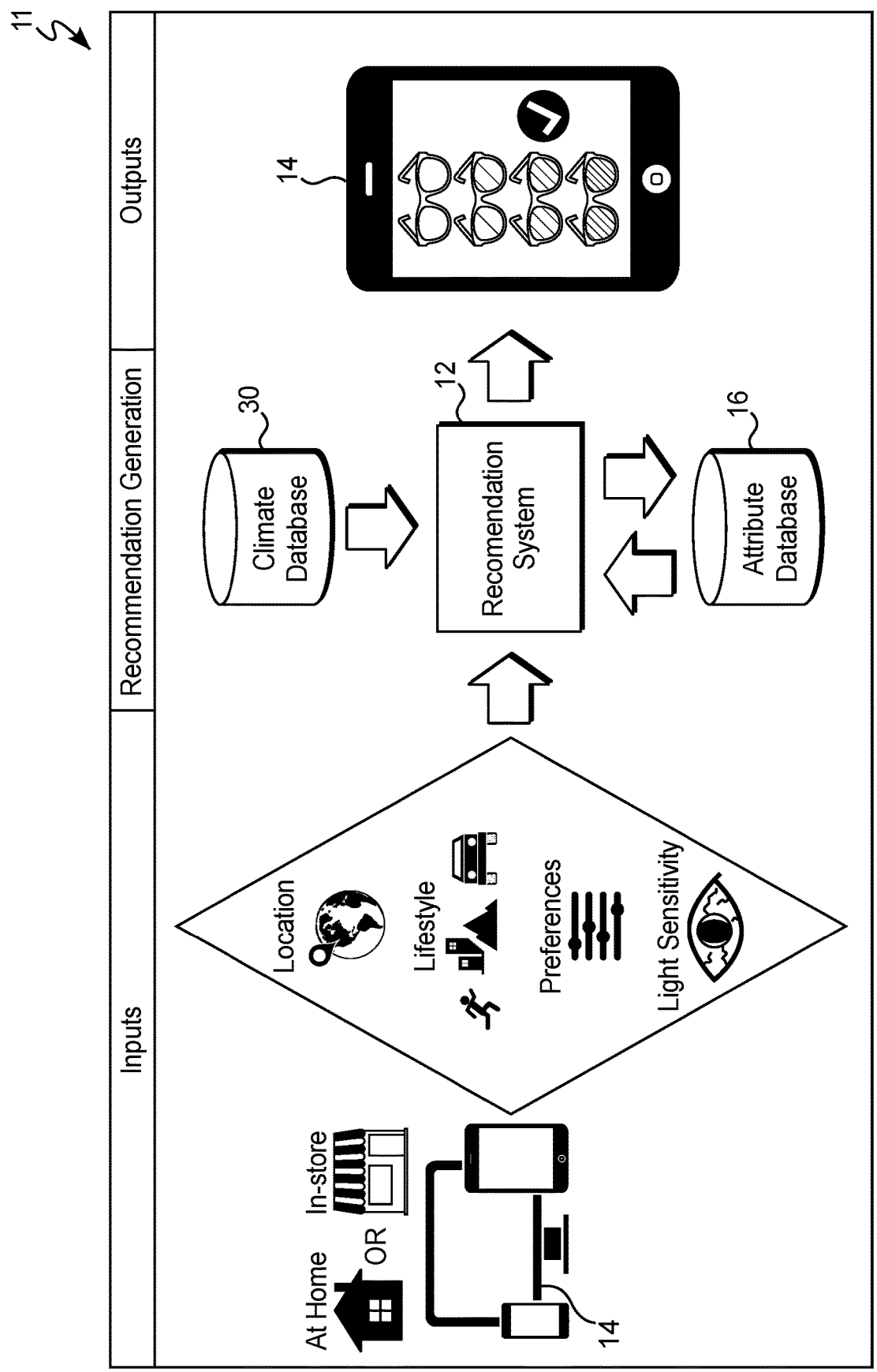
FIG. 2 shows a system for generating a customized photochromic optical article recommendation for a user.

Referring to FIGS. 1 and 2, systems 10, 11 for generating a customized photochromic optical article recommendation for a user are shown. The photochromic optical article may include an optical article or element or device that can be chosen from: ophthalmic articles, elements and devices; display articles, elements and devices; windows; mirrors; or active and passive liquid crystal cell articles, elements and devices. In some non-limiting examples, the photochromic optical article is a lens. The system 10, 11 may include a recommendation system 12 in communication with a computing device 14 and/or an attribute database 16.

With continued reference to FIGS. 1 and 2, the computing device 14 may include a display and an input device (e.g., a keyboard, a touchscreen, or the like) to allow a user (e.g., a consumer of a photochromic optical article) to input data into the computing device 14, which data may be communicated to the recommendation system 12. The computing device 14 may be a user-owned computing device 14, such as a smartphone, tablet computer, other mobile or non-mobile computer, and the like. The computing device 14 may be an in-store kiosk or other computing device 14 at a merchant location, such as a merchant associated with photochromic optical articles, such as a retail location, an optometrist office, and the like.

The data input to the computing device 14 and communicated to the recommendation system 12 may include location data. The location data may include a geographic location associated with a user, such as a location where the user resides or spends a sufficient amount of time (such as on vacation, a second residence, work travel, and the like). The user location data may be input to the computing device 14 by the user inputting a name of the location, coordinates associated with the location, identifying the location on a map displayed by the computing device, or other sufficient means. The user location data may be generated by the computing device 14 based on GPS data or other location data collected by the computing device 14. Multiple locations may be input as the location data. The user location data may be input to the computing device 14 in response to questionnaire data inquiring about a location(s) associated with the user.

With continued reference to FIGS. 1 and 2, the location data may be used by the recommendation system 12 to determine a living environment associated with the user. The living environment may include at least one of outdoor air temperature, exposure to radiation, or a combination thereof expected to be experienced by the user at the location associated with the user. Radiation may include at least one of UVA, UVB, blue light, visible light, infrared light, or any combination thereof. The living environment for the user location may be determined through testing and/or based on statistics for the location already known. Databases and modeling software like Cesora, Solargis, or the National Renewable Energy Laboratory (NLRE) may be used for this purpose. Thus, the user's exposure to UVA, UVB, blue light, visible light, infrared light, temperature, and the like, on a daily, weekly, monthly, seasonally, or yearly basis may be determined. The average of these factors over the course of a year may be considered, and/or the average over a portion of the year. For example, the average maximum outdoor air temperature over the 12 months of the year for a location may be used. The average maximum outdoor air temperature during a portion of the year, such as the 3, 4, 5, 6, 7, 8, 9, 10, or 11 warmest or coldest months of the year may also be used. The maximum average outdoor air temperature may be used for the entire year or a portion of the year to more closely represent daylight temperatures, which are the temperatures when the photochromic optical article will darken from exposure to actinic radiation. Additionally, the difference between the warmest eight months' maximum outdoor air temperature and the average maximum outdoor air temperature for the entire year may be useful for separating the needs of more consistent coastal regions from the greater temperature variability needs of a continental region. The type of outdoor air temperature average for the location to be considered during the recommendation generation may be chosen based on any number of other factors.

The data input to the computing device 14 and communicated to the recommendation system 12 may include lifestyle data. Lifestyle data may be input in response to questionnaire data inquiring about a lifestyle of the user. Lifestyle data may include factors such as time spent outdoors or indoors, occupation, common activities/hobbies of the user, common travel locations, or other information indicative of the environment in which the photochromic optical articles may be used.

The data input to the computing device 14 and communicated to the recommendation system 12 may include feedback data associated with preferences of the user in response to questionnaire data. The computing device 14 may be configured to display questionnaire data associated with performance attributes associated with photochromic optical articles. The questionnaire data may include questions associated with the relative importance the user places on each of the performance attributes.

Non-limiting examples of such performance attributes include at least one of the following: outdoor darkness, indoor clarity, speed to dark, speed to clear, indoor blue light protection, outdoor blue light protection, ultraviolet radiation protection, reactivity in indirect sunlight, time-based performance, in-car activation, and color consistency. The following Table 1 describes each performance attribute and the test associated with determining each performance attribute.

W Xenon arc lamp optical bench with a 50:50 beam splitter and the irradiance through a KG2 filter providing UVA/VIS, and the second beam having a KG2 filter and GG400 filter resulting in only supplemental VIS to provide 50 klux VIS and 6.7 W/m² UVA. A Zeiss M601 spectrophotometer measured the photopic transmittance % after 15 minutes of activation at 23° C. and 35° C.

Indirect Sunlight Test: The photochromic optical articles were activated in a similar fashion compared to the outdoor darkness composite test except with a Schott 320 nm LP filter instead of the KG2 filter and a Ashahi 395 nm LP in place of the GG400 filter to provide an irradiance spectral profile that more closely matches that of indirect lighting with the UVA at 6.6 W/m² and the VIS at 30 klux. A Zeiss M601 spectrophotometer measured the photopic transmittance % after 15 minutes of activation at 30° C.

Speed to Clear Composite Test: The photochromic optical articles were activated as described above in the outdoor darkness test at 23° C. and then the activation shutter was closed and the transmittance was collected over time to determine when the photopic transmittance reached 70% T

TABLE 1

| Performance Attribute | Attribute Description | Test Method |
| --- | --- | --- |
| Indoor Clarity | The optical article is clearer when indoors | Indoor Clarity Test: Bleached T % |
| Outdoor Darkness | The optical article is darker when outdoors in the sun | Outdoor Darkness Composite Test: T % @ 23° C. & @ 35° C. |
| Reactivity in Indirect Sunlight | The optical article reacts better (getting darker) in indirect sunlight (e.g., when not facing the sun) | Indirect Sunlight Test: T % with indirect sunlight @ 30° C. |
| Speed to Clear | The optical article changes back to clear faster when returning indoors from outdoors | Speed to Clear Composite Test: Time to 70% T @ 23° C. & T % after 30 min fade @ 10° C. |
| Speed to Dark | The optical article darkens faster when going outdoors | Speed to Dark Test: Time to 18% T |
| Indoor Blue Light Protection | The optical article offers better protection against harmful blue light indoors from screens and artificial lights | Indoor Blue Light Test: Indoor % blue cut |
| Outdoor Blue Light Protection | The optical article offers better protection against harmful blue light outdoors from the sun | Outdoor Blue Light Test: Outdoor % blue cut |
| Ultraviolet Radiation Protection | The optical article offers better protection against ultraviolet rays | UV Blocking Test: UVA & UVB blocking |
| Time-Based Performance | The optical article works better over time with less deterioration in how it reacts to light | Time-Based Test: Phototopic loss after 1 cycle fatigue |
| In-Car Activation | The optical article gets darker when driving | In-Car Test: BWS T % |
| Color Consistency | When changing back to clear, the optical article's color stays more consistent as it fades | Color Consistency Test: Area of the color during the fade back |

The test protocol associated with the test methods listed in Table 1 are provided below.

Indoor Clarity Test: Photochromic optical articles were pre-conditioned in each test to achieve full unactivated state by 5 minutes activation with 365 nm ultraviolet lamp followed by heating to 70° C. and exposure to yellow fluorescent lamp for 25 minutes followed by storage in the dark for at least 1 hour. The bleached photopic transmittance % was read using a Hunter UltraScan Pro. Photopic transmittance %, as used herein, refers to the spectral weighted transmittance associated with the vision of the eye under well-lit conditions and defined by the 1931 CIE photopic luminosity function.

Outdoor Darkness Composite Test: The photochromic optical articles were activated for 15 minutes in a two 150 occurs at 23° C. Linear interpolation between the adjacent two data points was used to derive the time to 70% T if 70% T was not exactly recorded at a measurement taken at a specific time. Using the same irradiance described in the outdoor darkness test above, the photochromic optical articles were activated for 15 minutes at 10° C., and the fade was collected for 30 minutes with the photopic transmittance % recorded at this time.

Speed to Dark Test: The photochromic optical articles were activated as described above in the outdoor darkness test at 23° C. and the photopic transmittance % over time was recorded to determine when 18% T occurs. During activation linear interpolation between the adjacent two data points were used to derive the time to 18% T if 18% T was not exactly recorded at a measurement taken at a specific time. This 18% T represents a category 3 lens darkness.

Indoor Blue Light Test: When tested in accordance with the 23° C. test above, the spectra at 5 nm increments from the first data measurement before the activation shutter opened were weighed in accordance with the weighting function in ISO 8980-3 Table B-1 from 280-460 nm and this integrated sum was reported.

Outdoor Blue Light Test: When tested in accordance with the 23° C. test above, the spectra at 5 nm increments from the spectra at 15 minutes immediately before the activation beam shutter closed were weighed in accordance with the weighting function in ISO 8980-3 Table B-1 from 280-460 nm, and this integrated sum was reported.

UV Blocking Test: Following the pre-conditioning described above, optical articles reported above, the spectra at 5 nm increments measured on a Cary 4000 spectrometer were weighted in accordance with the weighting functions in ISO 8980-3 Table B-1 from 280-315 nm for UVB and 315-380 nm for UVA, and these integrated sums were reported.

Time-Based Test: The photochromic optical articles were pre-conditioned as reported above in connection with the Indoor Clarity Test and in water at 100° F. on a single 300 W Xenon lamp with KG2 filter at 18 W/m² UVA. The change in photopic optical density (Absorbance) was recorded. The photochromic optical articles were then exposed to 0.25 W/m² at 340 nm for 65 hours of constant exposure in an Atlas Ci5000 Weatherometer. The lenses were again pre-conditioned and then measured again on the single lamp bench and the % photopic optical density loss was the difference between the initial change in optical density and this change after exposure divided by the initial change in optical density.

In-Car Test: The photochromic optical articles were pre-conditioned as reported above in connection with the Indoor Clarity Test and activated using one 150 W lamp on the A-BMP with a KG2 filter and a windshield filter in place and the irradiance adjusted to 1.0 W/m² integrated between 380-420 nm, 1.7 klux while at 27° C. The windshield glass consisted of a 2 plates of 2.3 mm Solar green glass with Solutia-UV enhanced polyvinylbutyrate as the laminate. The photopic transmittance % after 15 minutes activation is reported.

Color Consistency Test: The a* and b* color coordinates were recorded during time increments during activation and fade at 23° C. and the respective area pixilated. Using a Wavemetrics program capable of distinguishing incorporated vs. external area, the pixilation incorporated was reported to provide a number consistent with the total incorporated area (the start point and finish point at 30 minutes of fade are closed with a straight line).

In response to the questionnaire data, the user may input the feedback data into the computing device 14. The feedback data may include user preferences as to relative importance of the various performance attributes. The computing device 14 may communicate the feedback data to the recommendation system 12.

The feedback data including the relative importance of the various performance attributes may be indicated by responding to specific questionnaire data from the recommendation system 12. The relative importance may be indicated by the user ranking each of the performance attributes relative to one another, such as by ordering the performance attributes from most to least important (or vice versa) and/or assigning a numerical importance to each performance attribute (e.g., an importance on a scale or 1-100). The relative importance may be indicated by a user indicating which performance attributes are important to the user and/or which performance attributes are not important to the user.

With continued reference to FIGS. 1 and 2, the data input to the computing device 14 and communicated to the recommendation system 12 may include user eye data. The user eye data may include data associated with optical characteristics associated with the eyes of the user. Optical characteristics may include shape and/or size of the user's eye or glare sensitivity of the user's eyes or vision. The user eye data may be input to the computing device 14 in response to questionnaire data inquiring about the eye of the user. The user eye data may include eye sensitivity data associated with how sensitive the user's eye is to certain types of radiation or certain situations involving the user encountering radiation. For example, the eye sensitivity data may include data as to how sensitive the user's eye is to bright sunlight, driving at night, bright indoor lights, lights from displays of computing devices, transition from indoor light to outdoor light or light to dark environments (and vice versa), and the like. A sensitivity questionnaire may be used to determine glare sensitivity, such as by using the De Boer Scale (1967) to determine the user's sensitivity to glare from "unbearable" to "just noticeable". Glare sensitivity may be assessed using ophthalmic device equipment, such as the Brightness Acuity Tester (BAT) (available from Marco Ophthalmic) to assess functional visual acuity in bright light environment and recovery of visual acuity and/or a wearable device, such as Lumiz™ 100 (Essilor Instruments) that objectively quantifies the level of an eye's sensitivity to light by testing simultaneously, the two eyes of the user and determine a light sensitivity threshold in different light environment. The data input to the computing device 14 and communicated to the recommendation system 12 may include user demographic data. The user demographic data may be input to the computing device 14 in response to questionnaire data inquiring about the demographics of the user. User demographic data may include age, sex, eye color and the like.

With continued reference to FIGS. 1 and 2, the computing device 14 may communicate the location data, lifestyle data, feedback data, user eye data, and/or the user demographic data to the recommendation system 12, which may, in response and based at least partially on the received data, generate a customized photochromic optical article recommendation for the user as described hereinafter.

With continued reference to FIGS. 1 and 2, the attribute database 16 may store data associated with the performance attributes associated with a plurality of photochromic optical articles. The data associated with the performance attributes may include measured and/or calculated data quantifying the performance attributes exhibited by the photochromic optical articles. The data associated with the performance attributes may be determined by laboratory tests and/or field tests described above corresponding to the various performance attributes. The attribute database 16 may store this data associated with the performance attributes for each respective photochromic optical article.

The attribute database 16 may also include historical feedback data associated with other users' responses (e.g., feedback data) to the previously-described questionnaire data associated with relative importance of the various performance attributes.

The feedback data received by the recommendation system 12 from the computing device 12 of the user may be stored in the attribute database 16 as further historical feedback data, such that the historical feedback data increases as more user-specific data is received over time. This may allow the recommendation system 12 to adjust its recommendations over time as more feedback data is accumulated.

With continued reference to FIGS. 1 and 2, the recommendation system 12 may determine the plurality of performance attributes for each of the plurality of photochromic optical articles. Determining the plurality of performance attributes may include the recommendation system 12 receiving (e.g., passively receiving or actively retrieving) the data associated with the performance attributes from the attribute database 16. Determining the plurality of performance attributes for each of the plurality of photochromic optical articles may also include the recommendation system 12 parsing and/or analyzing this data received from the attribute database 16.

In response to determining the performance attributes, the recommendation system 12 may generate a compatibility score for each of the plurality of photochromic optical articles. The compatibility scores may initially be determined based at least partially on the historical feedback data (of other users) to the previously-described questionnaire data associated with relative importance of the various performance attributes or may be determined based only on the user's feedback data without consideration to the historical feedback data. The historical feedback data may be used to generate initial relative weights associated with the various performance attributes based on how historical users have weighted those performance attributes. All historical feedback data or only a segment of historical feedback data may be used to generate the initial weights. The segment of historical feedback data may be associated with users similar to the current users for whom the recommendation is being generated, such as a user with similar location data, lifestyle data, feedback data, user eye data, and/or user demographic data. The initial weights may be used to generate an initial compatibility score based on an algorithm using the results of the various performance attributes exhibited by the photochromic optical articles. This initial compatibility score may be used to generate the user compatibility score by including in the algorithm the user specific feedback data to account for specific user preferences with respect to the performance attributes (e.g., as compared to the historical feedback data). The feedback data provided by the user may be used to generate relative weights and/or adjust the initial weights associated with the various performance attributes, such that the outcome of the algorithm (e.g., the compatibility score) reflects the user's preferences provided by the feedback data.

Referring to FIG. 2, the compatibility score may be further modified based on the location data received by the recommendation system 12. Based on the location data, the recommendation system 12 may determine a living environment associated with the user. Based on the determined living environment of the user, the recommendation system 12 may communicate with a climate database 30 storing data associated with performance of each of the plurality of photochromic optical articles in specific geographic areas and/or climates.

The performance of each of the plurality of photochromic optical articles in specific areas or climates may be determined by testing the various photochromic optical articles in real-life outdoor environmental conditions at different areas and/or climates. As used herein, an area refers to a geographic location. The geographic location may be of any size, depending on the specificity with which the environmental conditions are to be determined. For instance, the area can be as small as a neighborhood or as large as a continent. An area may refer to a village, city, state, country, set of countries, specific region within a continent, or any other geographic spatial area. An area may also refer to proximate inter-country or inter-continental regions, which share similar environmental conditions. An area may also refer to geographic areas that share the same global latitude or longitude. An area may also refer to geographic areas sharing the same altitude. As used herein, climates refers to average weather conditions in a region over a long period of time. For instance, the climate can be classified as tropical, dry, temperate, continental, polar, and the like. As used herein, environmental conditions refer to conditions related to climate. Non-limiting examples of environmental conditions include outdoor air temperature, percent humidity, time of day, albedo, sky conditions, global irradiance, directional irradiance, air pressure, precipitation, wind, or any other measurable climactic variable or combination thereof.

Sky conditions of an area may include sunny, cloudy, partly cloudy, rainy, snowy, foggy, dark, or any combination thereof, at the time of testing. The outdoor air temperature may include an average outdoor air temperature throughout a year or a portion of a year. The average outdoor air temperature may include the average outdoor maximum air temperature over the 3 to 11 warmest or coldest months of the year. For example, the average outdoor air temperature may include the average outdoor maximum air temperature over the 4 to 10 warmest or coldest months. For example, the average outdoor air temperature may include the average outdoor maximum air temperature over the 5 to 9 warmest or coldest months. For example, the average outdoor air temperature may include the average outdoor maximum air temperature over the 6 to 8 warmest or coldest months. Global irradiance may be measured by placing a six-inch (15.2 centimeter) sphere having nearly ideal cosine response measuring almost a full angle of 180° on a spectroradiometer. Measurements may be made with the sphere pointing directly up towards the sky at a level of approximately three feet (0.91 meters) off the ground to measure irradiance. Global irradiance may include, non-exclusively, global irradiance in a 360 to 430 nm range. Directional irradiance may be measured using a two-inch (5.1 centimeter) integration sphere placed on a spectroradiometer. The sphere measures approximately ±45° of port normal. Directional irradiance may include directional irradiance in a 360 to 430 nm range.

During testing of photochromic optical articles to determine the environmental conditions for an area and performance of the photochromic optical articles in those conditions, these variables can be recorded at the time of testing. This recorded data can be used to determine both characteristics of the photochromic optical articles being tested and typical environmental conditions for the area.

Testing of the various photochromic optical articles may be performed at any number of areas or climates throughout the globe to determine, with the desired degree of specificity, the behavior of the various photochromic optical articles in different types of environments. The photochromic optical articles may be tested at any number of areas of different latitude, longitude or altitude. The photochromic optical articles may be tested at any number of geographic areas listed above. For instance, the photochromic optical articles may be tested in cities (or other areas) in which the photochromic optical articles are commonly used by users and having various levels of reflections of irradiance from surrounding buildings or trees.

Figures 3A, 3B, 3C:
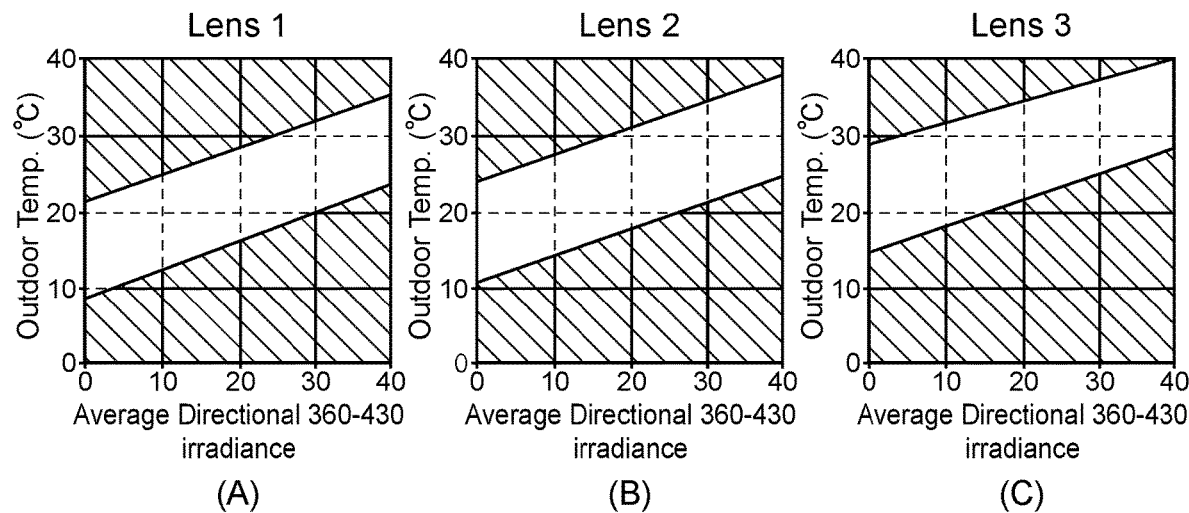
FIG. 3A-3C show plots of outdoor temperature versus average directional 360-430 irradiance ($W/m^2$) to provide a photopic transmittance of 10-20% (white area) calculated by a model generated from data collected for three different lenses.

Referring to FIGS. 3A-3C, the performance of the photochromic optical articles in specific areas or climates may be determined by generating a plot of outdoor temperature versus average directional 360-430 irradiance (W/m²) for each optical article which includes a photopic transmittance % band for each lens. The photopic transmittance % may be determined for each of the photochromic optical articles based on the testing described above. The photopic transmittance % may be determined based on a prediction model. Thus, each product has a specific optimum range of performance that assures the product is not too light for the viewing conditions or too dark for the viewing conditions.

The prediction model may be based on at least one of the following: incident irradiance of the optical article facing at least one direction, surface temperature of the optical article facing at least one direction, spectra of the optical article facing at least one direction, global irradiance of the area, environmental conditions of the area, or any combination thereof.

Incident irradiance, as used herein, means the irradiance as collected with the two-inch (5.1 centimeter) integrating sphere collinearly facing the direction of the optical article. Irradiance measurements may be made using any sufficient means. Irradiance measurements may be made using a spectroradiometer, such as an OL-756 spectroradiometer that records data from 200-800 nm, which can be used to determine spectral data for radiation, such as UVA, UVB, UVC, visible, and 360-430 nm range radiation for activation. To determine global irradiance of the area, the six-inch (15.2 centimeter) global collection sphere may be placed on the spectroradiometer. After the spectroradiometer is permitted to warm up for the appropriate time and sufficiently calibrated in accordance with manufacturer's directions, the global irradiance measurement may be taken and recorded. Several global irradiance measurements of the area may be taken within shorter or longer intervals of one another. To determine the incident irradiance for each of the photochromic optical articles being tested, the six-inch (15.2 centimeter) collection sphere may be removed and replaced with a two-inch (5.1 centimeter) collection sphere. The incident irradiance for at least one direction for each optical article may then be measured using the spectroradiometer. The incident irradiance of the photochromic optical articles may be taken after the photochromic optical articles have been allowed to darken fully from exposure to actinic radiation from the outdoor conditions.

Surface temperature, as used herein, may be measured by holding an infrared temperature gun proximate each optical article facing at least one direction to take the temperature measurement. The infrared temperature gun may be held several inches, such as 1-12 inches (2.5-30.5 centimeters), such as 3-9 inches (7.6-22.9 centimeters), or such as 4-6 inches (10.2-15.2 centimeters) from the optical article and the temperature determined and recorded.

Spectrum, as used herein may be determined using the spectrometer. The spectrum refers to the light transmitted through the lens facing at least one direction in the visible wavelength range (380-800 nm).

Multiple incident irradiances, surface temperatures, and spectra may be determined for each optical article with the optical article facing different directions (e.g., towards the sun, away from the sun, and the like).

The prediction model may generate a predicted photopic transmittance % based on the input of outdoor temperature and average directional irradiance, such as the directional irradiance in the 360-430 nm range (e.g., photopic transmittance % may be written as a function of outdoor temperature and average directional irradiance based on the data as shown in FIGS. 3A-3C). This model may allow prediction of photopic transmittance % of the optical article based on the outdoor temperature and average directional irradiance for any area (even those not tested) so as to determine whether an optical article is suitable for that area. A statistical software may be used to generate the prediction model. The prediction model may show a target photopic transmittance % of the photochromic optical articles based on certain combinations of outdoor temperature and directional irradiance, such that a target of 5-50% photopic transmittance, such as 10-20%, 10-15%, 15-20%, 5-25%, or 5-20%, is shown as a function of outdoor temperature and directional irradiance. The photopic transmittance % is based on the optical article being darkened from exposure to actinic radiation.

With continued reference to FIGS. 3A-3C, exemplary plots are shown of outdoor temperature versus average directional 360-430 irradiance (W/m²) for several different photochromic optical articles (Lenses 1-3). The plots include bands (white area) indicating a photopic transmittance % between 10-20% for each of Lens 1-3 to indicate the conditions of outdoor temperature and average directional irradiance at 360-430 nm for which each particular lens may be suitable for use by a user. In this non-limiting example, 10-20% photopic transmittance % is assumed to be the comfort range for a user, although this range may be adjusted. As can be seen in FIGS. 3A-3C, the white band for lenses 1 and 2 indicates that these lenses may be more suitable for areas or climates in which a lower outdoor temperature is associated, while lens 3 may be more suitable for areas or climates in which a higher outdoor temperature is associated. These predictions of photopic transmittance % for the various photochromic optical articles may be stored in the climate database 30 (from FIG. 2) and used to modify the compatibility score.

Therefore, from the above-described testing, the performance of each of the plurality of photochromic optical articles in specific areas or climates may be determined. Based on the living environment of the user and the performance of each of the plurality of photochromic optical articles at areas or climates similar to those of the user from the climate database 30, the recommendation system 12 may adjust the compatibility score to provide a more suitable recommendation of a photochromic optical article for the user.

The compatibility score may be further modified based on the lifestyle data received by the recommendation system 12. For example, for a user spending more time outdoors, the compatibility score may be adjusted by the recommendation system 12 to correspond to an optical article that provides darker characteristics when exposed to actinic radiation (better radiation protection) based on the user's expected increased time exposed to such radiation. Therefore, the optical article for a user may be recommended based, at least in part, on the lifestyle data of the user.

The compatibility score may be further modified based on the user eye data received by the recommendation system 12. For example a highly glare-sensitive user may be most comfortable and/or efficient with a photopic transmittance which is selected below the photopic transmittance level that would be required normally by the living environment for example: 15%-20% instead of 20%-25%, 10%-15% instead of 15%-20%, and 5%-10% instead of 10-15%. Therefore, the optical article for a user may be recommended based, at least in part, on the user eye data.

The compatibility score may be further modified based on the user demographic data received by the recommendation system 12.

Based on the compatibility scores generated by the recommendation system 12, the recommendation system 12 may generate a recommendation comprising at least one of the plurality of photochromic optical articles. The recommendation system 12 may provide the user with the photochromic optical article(s) most compatible with the user, such that the recommendation is customized to that user. The recommendation system 12 may communicate the recommendation to the computing device 14. The communicated recommendation may include the product name(s) associated with the most compatible photochromic optical article(s). The communicated recommendation may include more detailed results showing the compatibility score associated with each of the plurality of photochromic optical articles. Based on the received recommendation, the user may view further information about the recommended photochromic optical article(s) (and the non-recommended photochromic optical articles) and may initiate a transaction, such as a payment transaction, for the desired and/or recommended photochromic optical article.

Figure 4:
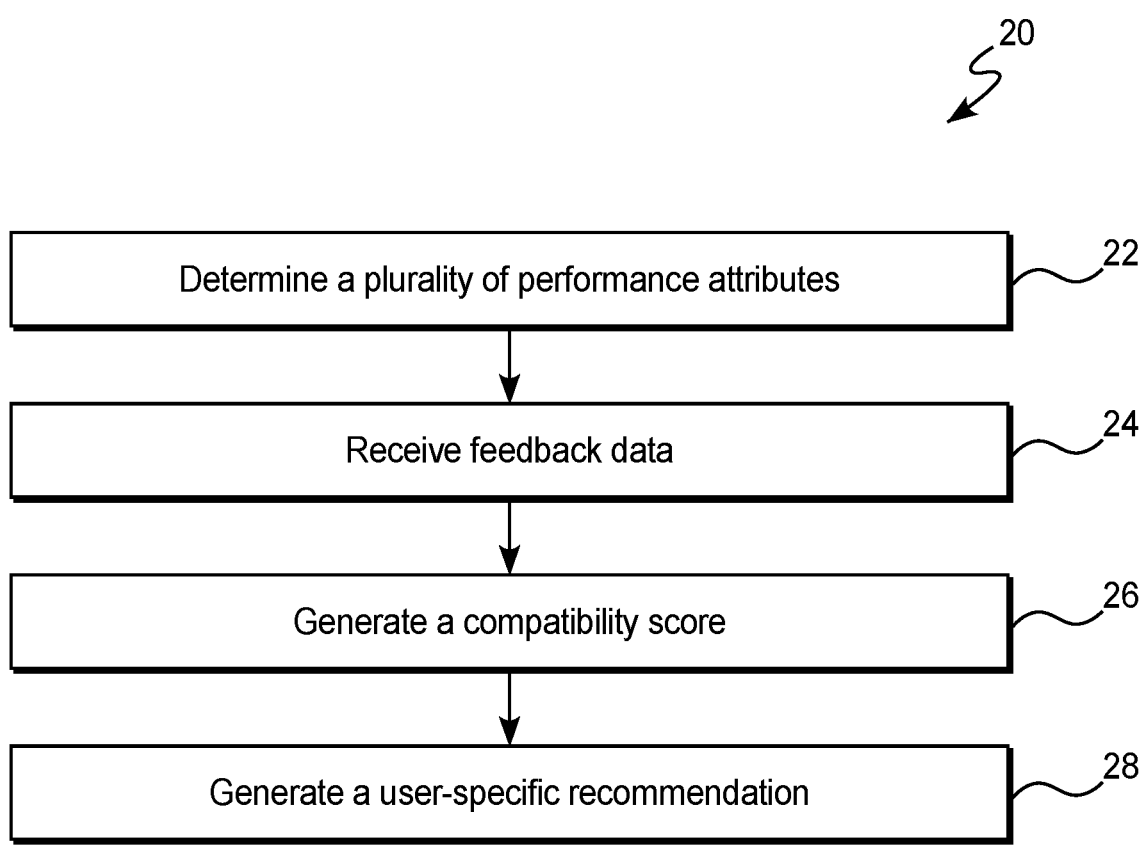
FIG. 4 shows a method for generating a customized photochromic optical article recommendation for a user.

Referring to FIG. 4, a method 20 is shown for generating a customized photochromic optical article recommendation for a user. At a first step 22, the method 20 may include the recommendation system 12 (from FIGS. 1 and 2) determining a plurality of performance attributes for each of a plurality of photochromic optical articles. At a second step 24, the recommendation system 12 may receive feedback data associated with each of the plurality of performance attributes from the user (via the computing device 14 (from FIGS. 1 and 2)). At a third step 26, based on the plurality of performance attributes and the feedback data, the recommendation system 12 may generate a compatibility score for each of the plurality of photochromic optical articles. At a fourth step 28, the recommendation system 12 may, based on the compatibility score for each of the plurality of photochromic optical articles, generate a user-specific recommendation comprising at least one of the plurality of photochromic optical articles.

A computer program product for generating a customized photochromic optical article recommendation for a user includes at least one non-transitory computer readable medium including program instructions that, when executed by at least one processor, cause the at least one processor to execute one of the previously-described methods. The at least one processor may include the recommendation system 12.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent ranges that are within the spirit and scope of the appended claims. For example, it is to be understood that the present invention contemplates, to the extent possible, one or more features of any embodiment can be combined with one or more features of any other embodiment.

The invention claimed is:

1. A method of generating a customized photochromic optical article recommendation for a user, comprising:
    for each of a plurality of photochromic optical articles, determining a plurality of performance attributes by conducting a laboratory and/or field test on each of the plurality of photochromic optical articles to determine measured and/or calculated data quantifying the plurality of performance attributes for each of the plurality of photochromic optical articles, the laboratory and/or field test for each of the plurality of optical articles being performed at a plurality of different geographic areas, each of the geographic areas having at least one different climate, latitude, longitude, altitude, or any combination thereof, the plurality of performance attributes comprising at least one of the following: outdoor darkness, indoor clarity, speed to dark, speed to clear, indoor blue light protection, outdoor blue light protection, ultraviolet radiation protection, reactivity in indirect sunlight, time-based performance, in-car activation, or color consistency;
    receiving, from a user device and with at least one processor, feedback data associated with each of the plurality of performance attributes, the feedback data comprising a relative importance of each of the plurality of performance attributes to the user;
    based on the measured and/or calculated data for each of the plurality of performance attributes and the feedback data, generating, with at least one processor and for each of the plurality of photochromic optical articles, a compatibility score, the compatibility score generated based an algorithm using parameters corresponding to the measured and/or calculated data for each of the plurality of performance attributes and a relative weight for each parameter based on the relative importance of each of the plurality of performance attributes to the user; and
    based on the compatibility score for each of the plurality of photochromic optical articles, generating, with at least one processor, a user-specific recommendation comprising at least one of the plurality of photochromic optical articles.

2. The method of claim 1, further comprising:
    determining, with at least one processor, a living environment associated with the user, wherein the compatibility score is based at least partially on the living environment associated with the user.

3. The method of claim 2, wherein the living environment associated with the user comprises at least one of outdoor air temperature and exposure to radiation.

4. The method of claim 1, further comprising:
    determining, with at least one processor, an optical characteristic associated with an eye of the user, wherein the compatibility score is based at least partially on the optical characteristic associated with the eye of the user.

5. The method of claim 4, wherein the optical characteristic associated with the eye of the user comprises a level of glare sensitivity of the user.

6. The method of claim 1, wherein each of the plurality of photochromic optical articles comprises at least one of the following: a lens, goggles, a visor, and a face shield.

7. A system for generating a customized photochromic optical article recommendation for a user, comprising:
    a database configured to store a plurality of performance attributes for each of a plurality of photochromic optical articles, the plurality of performance attributes determined by conducting a laboratory and/or field test on each of the plurality of photochromic optical articles to determine measured and/or calculated data quantifying the plurality of performance attributes for each of the plurality of photochromic optical articles, the laboratory and/or field test for each of the plurality of optical articles being performed at a plurality of different geographic areas, each of the geographic areas having at least one different climate, latitude, longitude, altitude, or any combination thereof, the plurality of performance attributes comprising at least one of the following: outdoor darkness, indoor clarity, speed to dark, speed to clear, indoor blue light protection, outdoor blue light protection, ultraviolet radiation protection, reactivity in indirect sunlight, time-based performance, in-car activation, or color consistency; and at least one processor programmed or configured to:
retrieve the plurality of performance attributes for each of a plurality of photochromic optical articles;
receive, from a user device, feedback data associated with each of the plurality of performance attributes, the feedback data comprising a relative importance of each of the plurality of performance attributes to the user;
based on the measured and/or calculated data for each of the plurality of performance attributes and the feedback data, generate, for each of the plurality of photochromic optical articles, a compatibility score, the compatibility score generated based an algorithm using parameters corresponding to the measured and/or calculated data for each of the plurality of performance attributes and a relative weight for each parameter based on the relative importance of each of the plurality of performance attributes to the user; and
based on the compatibility score for each of the plurality of photochromic optical articles, generate a user-specific recommendation comprising at least one of the plurality of photochromic optical articles.

8. The system of claim 7, wherein the at least one processor is further programmed or configured to:
determine a living environment associated with the user, wherein the compatibility score is based at least partially on the living environment associated with the user.

9. The system of claim 8, wherein the living environment associated with the user comprises at least one of outdoor air temperature and exposure to radiation.

10. The system of claim 7, wherein the at least one processor is further programmed or configured to:
determine an optical characteristic associated with an eye of the user, wherein the compatibility score is based at least partially on the optical characteristic associated with the eye of the user.

11. The system of claim 10, wherein the optical characteristic associated with the eye of the user comprises a level of glare sensitivity of the user.

12. The system of claim 7, wherein each of the plurality of photochromic optical articles comprises at least one of the following: a lens, goggles, a visor, and a face shield.

13. A computer program product for generating a customized photochromic optical article recommendation for a user, the computer program product comprising at least one non-transitory computer-readable medium including one or more instructions that, when executed by at least one processor, cause the at least one processor to:
retrieve a plurality of performance attributes for each of a plurality of photochromic optical articles, the plurality of performance attributes determined by conducting a laboratory and/or field test on each of the plurality of photochromic optical articles to determine measured and/or calculated data quantifying the plurality of performance attributes for each of the plurality of photochromic optical articles, the laboratory and/or field test for each of the plurality of optical articles being performed at a plurality of different geographic areas, each of the geographic areas having at least one different climate, latitude, longitude, altitude, or any combination thereof, the plurality of performance attributes comprising at least one of the following: outdoor darkness, indoor clarity, speed to dark, speed to clear, indoor blue light protection, outdoor blue light protection, ultraviolet radiation protection, reactivity in indirect sunlight, time-based performance, in-car activation, or color consistency;
receive, from a user device, feedback data associated with each of the plurality of performance attributes, the feedback data comprising a relative importance of each of the plurality of performance attributes to the user;
based on the measured and/or calculated data for each of the plurality of performance attributes and the feedback data, generate, for each of the plurality of photochromic optical articles, a compatibility score, the compatibility score generated based an algorithm using parameters corresponding to the measured and/or calculated data for each of the plurality of performance attributes and a relative weight for each parameter based on the relative importance of each of the plurality of performance attributes to the user; and
based on the compatibility score for each of the plurality of photochromic optical articles, generate a user-specific recommendation comprising at least one of the plurality of photochromic optical articles.

14. The computer program product of claim 13, wherein the one or more instructions cause the at least one processor to:
determine a living environment associated with the user, wherein the compatibility score is based at least partially on the living environment associated with the user.

15. The computer program product of claim 14, wherein the living environment associated with the user comprises at least one of outdoor air temperature and exposure to radiation.

16. The computer program product of claim 13, wherein the one or more instructions cause the at least one processor to:
determine an optical characteristic associated with an eye of the user, wherein the compatibility score is based at least partially on the optical characteristic associated with the eye of the user.

17. The computer program product of claim 16, wherein the optical characteristic associated with the eye of the user comprises a level of glare sensitivity of the user.

18. The computer program product of claim 13, wherein each of the plurality of photochromic optical articles comprises at least one of the following: a lens, goggles, a visor, and a face shield.

* * * * *